United States Patent [19]

Wortel et al.

[11] 4,400,567

[45] Aug. 23, 1983

[54] OXIDATIVE COUPLING OF AROMATIC METHYL GROUPS

[75] Inventors: Theodorus M. Wortel, Moerkapelle; Jan H. Schutten, Hellevoetsluis, both of Netherlands

[73] Assignee: Exxon Research & Engineering Co., Florham Park, N.J.

[21] Appl. No.: 419,751

[22] Filed: Sep. 20, 1982

[30] Foreign Application Priority Data

Sep. 23, 1981 [GB] United Kingdom ................. 8128748

[51] Int. Cl.$^3$ ........................... C07C 3/14; C07C 3/12
[52] U.S. Cl. ................................... 585/428; 585/422; 585/426; 585/471
[58] Field of Search .............. 585/422, 426, 427, 428, 585/429, 471, 470

[56] References Cited

U.S. PATENT DOCUMENTS

| 4,243,825 | 1/1981 | Williamson et al. | 585/428 |
|---|---|---|---|
| 4,254,293 | 3/1981 | Tremont et al. | 585/428 |
| 4,255,602 | 3/1981 | Tremont et al. | 585/428 |
| 4,255,603 | 3/1981 | Williamson et al. | 585/428 |
| 4,255,604 | 3/1981 | Williamson et al. | 585/428 |

FOREIGN PATENT DOCUMENTS

| 2944477 | 5/1981 | Netherlands. |
|---|---|---|
| 1488571 | 10/1977 | United Kingdom. |
| 1538670 | 1/1979 | United Kingdom. |

OTHER PUBLICATIONS

Lewis et al., Chemistry and Industry, (1953) 897.
Ledwith et al., J.C.S. Chem. Communication, (1974), 291,292.
Rasmussen et al., Makromol. Chem., 182, 701-703 (1981).
Rasmussen et al., J. Am. Chem. Soc., 103, 730 (1981).

Primary Examiner—Delbert E. Gantz
Assistant Examiner—A. Pal
Attorney, Agent, or Firm—Rebecca Yablonsky

[57] ABSTRACT

Highly selective oxidative coupling of aromatic methyl groups, such as coupling toluene to DPE, is effected under mild, liquid phase conditions with a peroxodisulfate without expensive metal ion catalysts, in presence of substantial amounts, preferably equimolar, of methyl, ethyl or benzyl substituted quaternary ammonium salts. A continuous process is possible by electrolytic regeneration of the spent oxidant.

10 Claims, 2 Drawing Figures

OXIDATIVE COUPLING OF AROMATIC METHYL GROUPS

This invention relates to oxidative coupling of aromatic compounds having methyl substituents to form diarylethanes, and in particular concerns selective coupling of toluene to produce 1,2-diphenylethane (hereinafter refered to as DPE).

The diarylethanes obtained by coupling of methyl-substituted aromatic compounds have a wide variety of applications depending on the substitution of the aromatic and ethane moieties. They may also be useful chemical intermediates. DPE is particularly interesting since it may be dehydrogenated to form stilbene which may be reacted with ethylene to form styrene, which is presently prepared in a two-step process in which benzene is alkylated to form ethylbenzene which is thereafter dehydrogenated to styrene.

The coupling of toluene to form DPE and/or stilbene has been described in vapour phase reactions carried out at high temperatures in the region of 400° to 600° C. over metal oxide catalysts. For example, U.K. Pat. No. 1538670 describes the use of bismuth oxide as catalyst in this vapour phase coupling. U.K. Pat. No. 1488571 employs metal oxide catalysts such as lead, cadmium and bismuth oxides. Other complex metal oxides for vapour phase catalysts are also described in U.S. Pat. Nos. 4,255,602, 4,255,603, 4,255,604, 4,254,293 and 4,243,825.

The chemical literature describes the oxidation of toluene in the liquid phase, and coupled products are mentioned, but these are produced as by-products along with significant amounts of uncoupled oxidation products such as aldehydes and acids. "Chemistry and Industry" 1953, pages 897-898 discloses metal-catalyzed persulphate oxidation of organic compounds and indicates that in an aqueous persulphate solution in the presence of silver ions toluene is oxidized to a mixture of benzaldehyde, benzoic acid and DPE. An article in JCS Chem. Comm., 1974, pages 291-292 describes heating aqueous-acetonitrile solutions of $S_2O_8^{2-}$ and toluene to produce a mixture containing 50% DPE, 30% benzaldehyde and 10% benzyl alcohol. DE 2944477 describes metal-catalysed peroxodisulphate oxidation of aromatic or hetero-aromatic methyl groups to form alcohols, aldehydes, carboxylic acids and dimeric or polymeric coupling products using a peroxodisulphate as oxidising agent and metal salt and/or complex compound catalysts. Phase transfer reagents and/or crown ethers can be used in the oxidation. Tetrabutyl ammonium bromide is exemplified in an oxidation of para-t-butyl-toluene that yields 5% dibenzyl.

Since the known processes produced coupled products only in a mixture containing large amounts of other monomeric oxidation products these reactions are unsuitable for consideration as a commercial route to coupled products such as DPE or stilbene. Furthermore the presence of metal salts as taught by the prior art may make the regeneration of persulphate by electrochemical means more difficult. Metal ions such as silver may interfere with persulphate regeneration by catalysing persulphate degradation during electrolysis. Furthermore metal ions present in an electrolyte could be deposited on the electrodes thereby hindering electrochemical regeneration.

It has now been found that highly selective couplings may be effected in a liquid phase oxidation by carrying out the coupling reaction in the presence of certain amounts of a phase transfer catalyst without the addition of metal compounds.

Thus, in one aspect this invention provides a process for the selective dehydrocoupling of a carbocyclic or heterocyclic, aromatic compound having a methylidyne group (—CH<) attached to the aromatic nucleus selectively to form dimeric products, in which process the aromatic compound is oxidatively coupled in the liquid phase with a peroxodisulphate in the presence of a methyl, ethyl or benzyl-substituted quaternary ammonium salt, there being at least 0.2 equivalents of quaternary ammonium cation per mole of the peroxodisulphate.

As used herein, the term "methylidyne group" is intended to include a methyl group, methylene groups (—CH$_2$—) as well as other methylidyne groups having two non-hydrogen substituents. Thus, the starting material may be a wide variety of aromatic compounds having a hydrogen atom in an alpha position relative to the aromatic nucleus. This nucleus may be, for example, a substituted or unsubstituted benzene, naphthalene or heterocyclic aromatic compound such is pyridine.

The preferred starting material is toluene, in which case the coupled product is DPE. However, the coupling may also be effected with toluenes bearing a variety of substituents on the benzene ring or on the methyl side chain which will result in a corresponding substituted DPE product.

The peroxodisulphate is generally most conveniently employed as an aqueous solution. The process of the invention then involves a reaction medium comprising at least two liquid phases: one organic phase containing the aromatic starting material, and one aqueous phase containing peroxodisulphate. It has surprisingly been found that the use of large amounts of certain quaternary ammonium salts promotes the oxidative coupling reaction rather than non-coupling oxidations and that, as discussed below, the same promotion is not seen with phase transfer catalysts in general. Thus, in the process of the invention, when the starting material is toluene coupling to form DPE is promoted:

$$[O] + 2C_6H_5CH_3 \rightarrow C_6H_5CH_2CH_2C_6H_5 + H_2O \quad (A)$$

rather than the competing oxidations of the methyl group to form benzaldehyde and benzoic acid, thus enabling DPE to be prepared with high selectivity.

The peroxodisulphate is generally the peroxodisulphate of an alkali metal or ammonium. Potassium and ammonium peroxodisulphate gives particularly good results. Where it is desired to reduce the amount of water present the more soluble ammonium peroxodisulphate may be used with advantage. In addition the electrolytic regeneration of ammonium peroxodisulphate is more readily accomplished with high current efficiencies, and ammonium peroxodisulphate is thus highly preferred.

Peroxodisulphate behaves as a pseudo-catalyst in the coupling reaction as in acting as an oxidant it is converted to the corresponding sulphate or bisulphate. For example:

$$2\ C_6H_5CH_3 + K_2S_2O_8 \longrightarrow C_6H_5CH_2CH_2C_6H_5 + 2KHSO_4 \quad (B)$$

toluene            DPE

The peroxodisulphate can be regenerated from the formed sulphate or bisulphate, and in a prefered aspect this invention employs continuous regeneration of peroxodisulphate from the bisulphates and sulphate formed in the rection mixture. Electrolytic methods of peroxodisulphate production and regeneration are well known in the art, and these known techniques may be adopted in regenerating peroxodisulphate for the present invention.

The quaternary ammonium salts which may be used in the invention are ethyl, methyl or benzyl substituted quaternary ammonium salts such as tetraethylammonium (TEA) salts, tetramethylammonium (TMA) salts and benzyl-trimethylammonium (BTMA) salts, and TMA and BTMA salts are particularly preferred. It is a particularly surprising feature of the invention that high selectivity to coupled products may be obtained with ammonium peroxodisulphate in conjunction with quaternary ammonium salts according to the invention since in the absence of such salts ammonium peroxodisulphate gives a poor yield of coupled products.

Quaternary ammonium salts are sometimes used as phase transfer catalysts, but in phase transfer catalysis it is normally expected that the catalytic ability of a quaternary tetraalkyl ammonium salt will increase as the size of the alkyl group increases at least up to a $C_4$ alkyl group (tetrabutylammonium), the activity then decreasing as the alkyl group increases further in size. In articles by Rasmusen et al in Makromol Chem 182, 701–703 (1981) and J.A.C.S. (1981),103,730 the free radical polymerization of butyl acrylate is described in the presence of potassium peroxodisulphate and a phase transfer catalyst. It is disclosed there that in phase transfer catalysed reactions, small quaternary ions are less effective than large ones. Rasmussen also indicates that more symmetrical quaternary ions are more effective.

Rasmussen further teaches the use of crown ethers as phase transfer catalysts. We have found surprisingly that TMA salts (with the smallest quaternary alkyl ammonium cation) and the assymetrical BTMA salts are much better in the selective coupling reaction of the invention than tetrapropylammonium (TPA) or tetrabutylammonium (TBA) salts. This indicates that the catalysis of the process of the invention is not phase transfer catalysis but a different mechanism. This is further demonstrated by the relatively lower selectivity to coupled products seen when a highly effective phase transfer catalyst such as a crown ether is used in place of the quaternary ammonium salt.

To reduce competitive salt effects in the coupling reaction and/or peroxodisulphate regeneration the anion in the quaternary ammonium salts is preferably sulphate. Particularly preferred phase transfer catalysts are therefore TMA sulphate and BMTA sulphate.

The phase transfer catalyst is employed in relatively large amounts, there being at least 0.2 equivalents of quaternary ammonium cation per mole of peroxodisulphate—thus, where the quaternary ammonium salt is formed with a divalent anion such as the sulphate ion, there is at least 0.1 mole of the divalent salt per mole of peroxodisulphate. Preferably at least 0.4 equivalents of quaternary ammonium cation per mole of oxidant are used, and particularly high selectivities has been achieved with from 1.0 to 8.0 equivalents of quaternary ammonium cation per mole of peroxodisulphate. Very preferably the quaternary ammonium cation is present in an amount of from 1.8 to 4.0 equivalents per mole of peroxodisulphate. It has also been found that as the amount of water is reduced selectivity to coupled products is reduced, but may be restored by a corresponding increase in the amount of quaternary ammonium salt. Thus, for example, in the presence of from 30 to 50 moles of water per mole of peroxodisulphate, high selectivities are obtained with from 1.8 to 2.0 equivalents of quaternary ammonium cation per mole of peroxodisulphate; if the amount of water is reduced to from 15 to 25 moles per mole of peroxodisulphate it has been found that similar selectivities are obtained by using from 3.6 to 4.0 equivalents of quaternary ammonium cation per mole of peroxodisulphate.

The coupling reaction is carried out at conditions in which the reactants are in the liquid phase. To obtain acceptable conversion with adequate selectivity to coupled products at atmospheric pressure, the reaction temperature is preferably between 50° C. and the reflux temperature of the reaction mixture. Sub- and superatmospheric pressures may be used and this enables a wider range of reaction temperatures to be employed in the liquid phase. Preferably the reaction is carried out at a temperature of from 75° to 150° C. It is usually most convenient to operate at reflux.

The reaction has been found to be promoted by efficient contact between the two liquid phases, and it is therefore advantageous to mix two phases thoroughly. Thus, the reaction mixture is preferably vigorously stirred.

The coupling reaction to give dimeric products stoichiometrically requires a mole ratio of aromatic starting material: peroxodisulphate of 2:1, as illustrated in equation B hereinbefore. It has been found that the process of the invention may be operated with good selectivity even when the starting materials are not in the stoichiometric ratio, and thus with either the aromatic starting material or the peroxodisulphate present in excess. However, the stoichiometric mole ratio of the aromatic starting material and peroxodisulphate of 2:1 is preferred.

It is a significant feature of the present invention that high conversions with good selectivity to coupled products may be achieved without requiring addition of a further metal ion catalyst and that the peroxodisulphate may readily be electrolytically regenerated from the spent reaction mixture in the presence of the quaternary ammonium salts. In fact, an increase in current efficiencies has been observed where regenerating spent peroxodisulphate solutions of the invention which contain quaternary ammonium salts.

Following the coupling reaction the reaction mixture may be cooled and the aqueous and organic phases recovered. The coupled products will be in the organic phase which can readily be recovered by conventional techniques. The coupled products can then be recovered from the organic phase by standard methods such as fractional distillation.

In a preferred aspect this invention provides a continuous process for the oxidative dehydrocoupling of aromatic compounds having a methylidyne group (—CH<) attached to the aromatic nucleus to form dimeric products coupled through the methylidyne groups of the constituent aromatic compounds, in which process:

(a) the aromatic compound having a methylidyne group is contacted with an aqueous peroxodisulphate solution in the presence of a methyl, ethyl or benzyl-substituted quaternary ammonium salt, preferably a TMA salt, TEA salt or BTMA salt, there being at least 0.2 equivalents of quaternary ammonium cation per mole of the peroxodisulphate to form a mixture of an organic phase comprising dimeric products and an aqueous phase comprising quaternary ammonium salts and reduced forms of the peroxodisulphate;

(b) separaing the organic and aqueous phases, and recovering the dimeric products from the organic phase:

(c) subjecting the aqueous phase to electrolysis to regenerate the peroxodisulphate therein; and (d) recycling the aqueous phase comprising regenerated peroxodisulphate and quaternary ammonium salt to step (a).

The invention is particularly concerned with coupling toluene to form DPE, and the DPE may thereafter be converted to styrene. Therefore in a further aspect this invention provides a process for the preparation of styrene, in which process toluene is coupled by the process described hereinbefore to form DPE, the formed DPE is dehydrogenated to stilbene, and the formed stilbene is reacted with ethylene to form styrene by metathesis.

The dehydrogenation of DPE to stilbene may be affected by a further oxidation, but it is preferred to carry out dehydrogenation by cracking over a dehydrogenation catalyst. Such cracking reactions are well known and it is believed to be within the competence of one skilled in the art to select appropriate conditions. By way of illustration, the dehydrogenation may be carried out at a temperature of from 400° to 800° C., preferably from 500° to 600° C. over a conventional alumina dehydrogenation catalyst. Steam dilution is preferably used and the weight ratio of steam:hydrocarbon feed may be from 2.5 to 4.0. Typically liquid hourly space velocities (LHSV) of from 0.1 to 10 $hr^{-1}$ are employed, and preferably a LHSV of 1.0 to 2.0 $hr^{-1}$ is employed.

If the ultimate object is to prepare styrene, the formed stilbene is then reacted with ethylene to form styrene by metathesis. The metathesis reaction has been described, for example, in U.S. Pat. No. 3,965,206, U.K Pat. No. 1488571 and in Chem. Tech., April 1978, page 244. Stilbene is reacted in the vapour phase with ethylene over a disproportionation catalyst at a temperature of from 300° to 600° C. The reaction is as follows:

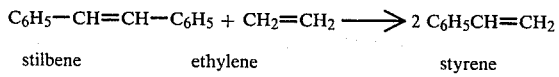

An alternative procedure is to effect the dehydrogenation and disproportionation in a single step by reacting DPE with ethylene over a suitable catalyst, for example as described in U.K Pat. No. 1538620.

Suitable disproportionating catalysts include those known to be effective in olefin disproportionation such as oxides of molybdenum, tungsten, vanadium, niobium, tantalum and rhenium, hexacarbonyl compounds and sulphides of tungsten and molybdenum. The catalytic materials may be associated with conventional carriers such as silica, alumina, zeolites, zirconia, thoria and titania. The catalyst may also include other active components, and may, for example, contain cobalt oxide or compounds of alkali metals or alkaline earth metals.

Disproportionation catalysts can be adversely affected by polar impurities and it is therefore desirable to treat the stilbene to remove such impurities. This may be achieved by passing the stilbene through an adsorbent material which selectively adsorbs the polar compounds. Certain silicas and aluminas may be used for this purpose. For example, stilbene may be passed through an adsorbent bed in the liquid phase at a temperature of from 70° to 210° C.

Alternatively, polar impurities may be removed by contact with a variety of reagents which will react and thus remove the polar components. For example, organometallic compounds or metal hydrides may be used by conventional techniques.

Further alternative purification procedures include crystallization, fractional distillation and solvent extraction.

The invention will now be described in more detail, though only by way of illustration with reference to the accompanying drawings, in which.

Figure 1:
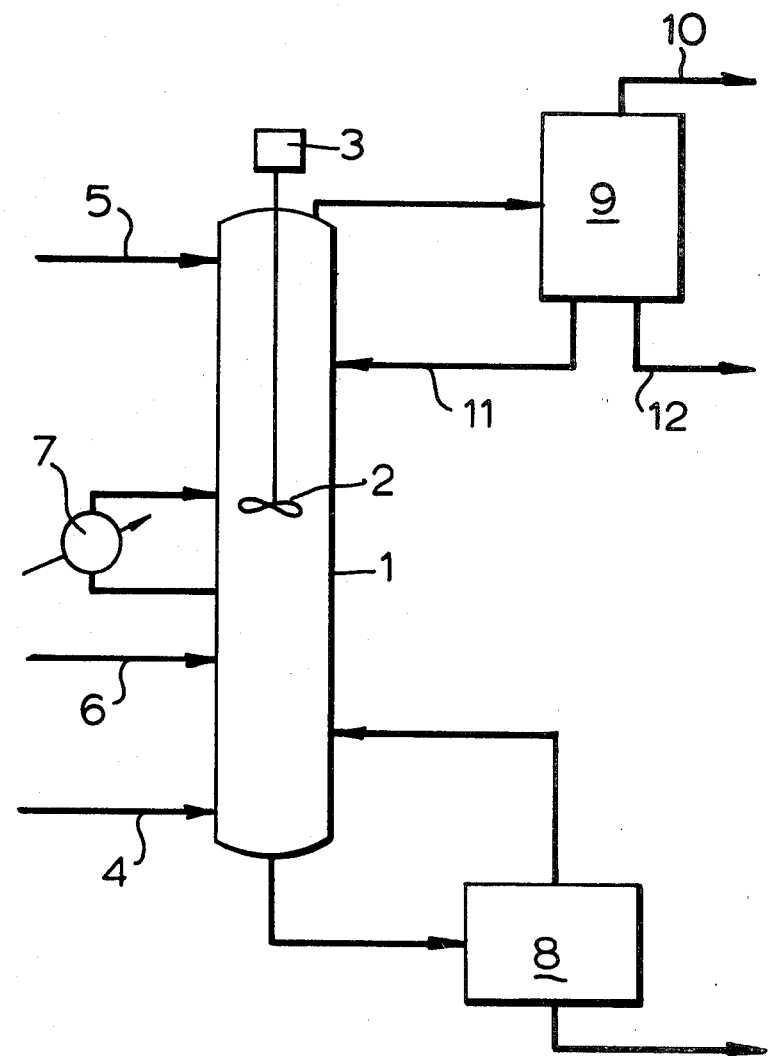
FIG. 1 is a flow diagram showing a preferred arrangement for preparing DPE from toluene according to the invention.

FIG. 1 shows a reactor vessel provided with a stirrer 2 driven by motor 3. Toluene is fed to the base of the reactor by feed line 4 and ammonium peroxodisulphate and the quaternary ammonium salt, for example TMA sulphate, are introduced by line 5. Solvent may be added, if desired through line 6. The reactor is provided with a heat exchanger 7.

Spent oxidant is withdrawn from the base of reactor 1 to a coalescer or settling drum 8, where organic liquids are separated and returned to the reactor. The recovered oxidant, containing some quaternary ammonium salt, peroxodisulphate, sulphate and bisulphate, is fed to the peroxodisulphate regeneration apparatus (not shown in FIG. 1). Regenerated peroxodisulphate may be reintroduced to reactor by line 5.

The reaction product containing unreacted toluene, DPE and oxidation products, such as benzaldehyde and benzoic acid, is taken to purification step 9. DPE is separated by and collected via line 10. Toluene may be collected separately or recyled to the reactor via line 11 as shown. Line 12 is a purge.

Figure 2:
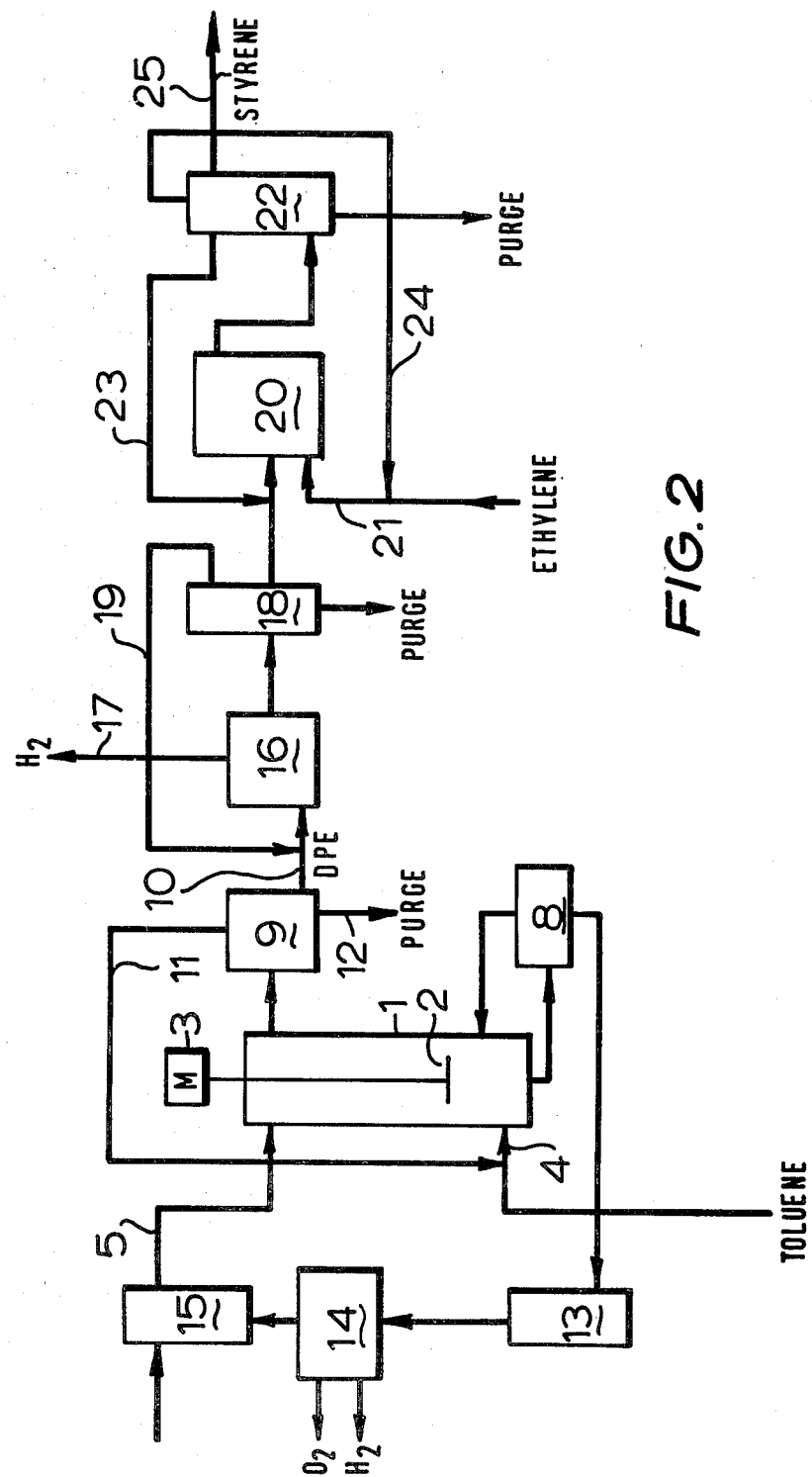
FIG. 2 is a flow diagram showing a system for preparing styrene from toluene.

FIG. 2 shows a similar reactor to that shown in FIG. 1 incorporated in a scheme for the preparation of styrene. The reactor is associated with a regeneration system in which spend oxidant recovered at 8 is fed to vessel 13 where the ph is adjusted. 14 is an electrochemical cell for regenerating peroxodisulphate which is then fed to a storage tank 15 where it is supplemented as necessary with fresh peroxodisulphate.

Purified DPE from the first stage is fed to a second reactor 16 where it is heated and passed over a dehydrogenation catalyst. Hydrogen is evolved and recovered at 17. The dehydrogenation product is fed to a purification stage 18. Here, unreacted DPE is recovered and recycled through line 19 to reactor 16. Stilbene is separated and purified by the removal of polar impurities, then fed to a metathesis reactor 20.

Ethylene is fed to reactor 20 via line 21. Within reactor 20 the etylene and stilbene are heated and passed over a disproportionation catalyst. Styrene is formed, and this is fed with unreacted starting materials to purification stage 22. Stilbene is recovered and recycled via 23. Ethylene is recovered and recycled via line 24. High purity styrene is collected via line 25.

The following examples are given, again by way of illustration only, to show some aspects of the invention in further detail and to compare the invention to prior art processes.

EXAMPLES 1-19: Toluene Coupling

Experiments on toluene coupling were carried out in a one liter conventional glass reactor vessel at atmospheric pressure. 44.6 g (0.165 mole) potassium peroxodisulphate, 35.0 ml (0.33 mole) toluene and 500 ml water were introduced into the reactor, in some instances together with an additive, and the reaction mixture was brought to reflux at 85° C. with vigorous stirring. Samples were taken at intervals timed from the commencement of reflux and the organic layer of these samples was separated and analysed in a gas chromatograph. Selectivity is measured as mole % of coupled products (i.e. stilbene and DPE) in the sample.

Comparative examples were provided by tests conducted with no additives, and with additions of tetrabutylammoniums (TBA) sulphate and salts of alkali metals, ammonium and silver. Examples of the invention were provided by tests run with the addition of tetraethylammonium (TEA) sulphate, and benzyltrimethylammonium (BTMA) sulphate.

The results obtained are set out in Table 1. Examples 16, 17 and 19 show that by employing the process of the invention higher conversion of toluene to coupled products is obtained than without additives (Comparative Examples 1 and 2) and this is obtained without the need for introducing further metal ions into the reaction mixture as in Comparative Examples 3 to 13. Comparative Example 15 shows that TBA sulphate which would be expected to be the optimum quaternary ammonium salt for effecting phase transfer catalysis actually results in lower conversion and lower selectivity to coupled products. Example 18 shows the extent of coupling (24% conversion with 51% selectivity to coupled products) which was measured at the start of reflux and thus before the reaction had proceded to completion. The conversion is even at that stage considerably higher than is seen after one hour reflux using TBA sulphate.

tive. Samples were taken after reaction times of 30, 60 and 120 minutes. The results are given in Table 2 and show a high selectivity to coupled products at high rates of conversion.

EXAMPLE 23-24: Toluene Coupling with TMA and TPA Additives

The procedure of Example 1 was repeated using different quarternary ammonium salts as additives. Example 23 is a comparative example which shows that TPA sulphate results in very low toluene conversion and poor selectivity to coupled products. By contrast in Example 24 according to the invention TMA sulphate gave highly selective production of coupled products. The results are given in Table 3.

TABLE 2

| Example | 20 | 21 | 22 |
|---|---|---|---|
| Time (min) | 30 | 60 | 120 |
| Toluene Conversion | 51.86 | 60.33 | 66.01 |
| Coupling | | | |
| Selectivity (mole %) | 94.00 | 93.00 | 92.00 |
| Styrene Precursors (wt %) | 47.62 | 55.06 | 60.19 |
| - DPE | 46.89 | 53.75 | 58.83 |
| - Stilbene | 0.73 | 1.31 | 1.36 |
| By-products (wt %) | 2.92 | 3.58 | 3.88 |
| - benzaldehyde | 2.72 | 3.40 | 3.72 |
| - benzylalcohol | 0.20 | 0.18 | 0.16 |
| - benzoic acid | 0.00 | 0.00 | 0.00 |
| Unidentified | 1.32 | 1.69 | 1.94 |

TABLE 3

| Example | 23 | 24 |
|---|---|---|
| Comparison/Invention | Comparison | Invention |
| Additive | 0.15 mole (TPA)$_2$SO$_4$ | 0.15 mole (TMA)$_2$SO$_4$ |
| Time (min) | 60 | 60 |
| Toluene Conversion (%) | 19 | 66 |
| DPE (wt %) | 5 | 55 |
| Benzaldehyde (wt %) | 11 | 6 |
| DPE Selectivity (mole %) | 64 | 87 |

TABLE 1

| Example Comparative | Additive (mol) | | Reaction Time (hr) | Toluene Conversion (%) | DPE (wt %) | Benz-aldehyde (wt %) | B.acid/B.aldehye (mole/mole) | Coupling Selectivity (mole %) |
|---|---|---|---|---|---|---|---|---|
| 1 | — | | 1 | 43.30 | 29.10 | 11.80 | 0.09 | 73 |
| 2 | — | | 2 | 47.50 | 33.40 | 13.10 | 0.13 | 73 |
| 3 | Na$_2$SO$_4$ | (0.03) | 2 | 53.82 | 38.08 | 11.69 | 0.15 | 78 |
| 4 | Na$_2$SO$_4$ | (0.30) | 2 | 54.07 | 35.00 | 13.37 | 0.20 | 74 |
| 5 | K$_2$SO$_4$ | (0.03) | 2 | 46.32 | 28.83 | 11.96 | 0.00 | 75 |
| 6 | K$_2$SO$_4$ | (0.30) | 2 | 54.03 | 37.56 | 11.47 | 0.003 | 80 |
| 7 | Cs$_2$SO$_4$ | (0.03) | 2 | 59.37 | 41.93 | 11.75 | 0.05 | 81 |
| 8 | Cs$_2$SO$_4$ | (0.15) | 2 | 55.61 | 42.20 | 10.66 | 0.05 | 82 |
| 9 | Cs$_2$SO$_4$ | (0.30) | 2 | 52.92 | 36.63 | 11.70 | 0.00 | 79 |
| 10 | FeSO$_4$ | (1.6 × 10$^{-3}$) | 1 | 46.60 | 27.97 | 13.32 | 0.09 | 69 |
| 11 | Mn(OAc)$_2$ | (1.6 × 10$^{-3}$) | 1 | 45.47 | 30.42 | 11.19 | 0.00 | 76 |
| 11 | AgNO$_3$ | (1.6 × 10$^{-3}$) | 0.5 | 52.20 | 42.38 | 10.22 | 0.00 | 82 |
| 12 | AgNO$_3$ | (7.7 × 10$^{-3}$) | RS | 49.40 | 31.21 | 13.02 | 0.00 | 74 |
| 13 | AgNO$_3$ | (7.7 × 10$^{-3}$) | 0.25 | 64.76 | 51.58 | 9.20 | 0.00 | 87 |
| 14 | (NH$_4$)$_2$SO$_4$ | (0.03) | 2 | 50.62 | 33.07 | 12.20 | 0.04 | 76 |
| 15 | (TBA)$_2$SO$_4$ | (0.15) | 1 | 9.00 | 5.80 | 0.60 | 0.17 | 66 |
| 16 | (TEA)$_2$SO$_4$ | (0.03) | 1 | 58.92 | 43.06 | 10.36 | 0.00 | 83 |
| 17 | (TEA)$_2$SO$_4$ | (0.15) | 1 | 66.66 | 58.18 | 4.23 | 0.00 | 94 |
| 18 | (TEA)$_2$SO$_4$ | (0.15) | RS | 24.01 | 9.80 | 11.05 | 0.00 | 51 |
| 19 | (BTMA)$_2$SO$_4$ | (0.15) | 1 | 52.00 | 44.40 | 4.70 | 0.00 | 85 |

Note:
RS = start to reflux

EXAMPLES 20-22: Toluene Coupling with TEA Additive

The procedure of Example 1 was repeated using 0.15 mole of tetraethylammonium (TEA) sulphate as addi-

EXAMPLES 25–27: TOLUENE COUPLING USING TMA ADDITIVE

The procedure of the previous Examples was repeated using 0.15 mole of TMA sulphate as additive, but the amount of toluene was halved so that the toluene:peroxodisulphate mole ratio was approximately 1:1. Samples were taken after reaction times of 15, 60 and 120 minutes. The results are given in Table 4 and show highly selective coupling takes place in the presence of TMA sulphate even when the amount of starting material present would be expected stoichiometrically to favour the monomolecular oxidation reaction to form products such as benzaldehyde.

TABLE 4

| Example of the Invention | 25 | 26 | 27 |
|---|---|---|---|
| Time (min) | 15 | 60 | 120 |
| Toluene Conversion (%) | 70.58 | 99.50 | 100.00 |
| Coupling Selectivity (mole %) | 92.00 | 78.00 | 79.00 |
| Styrene Precursors (wt %) | 62.93 | 77.20 | 77.32 |
| - DPE | 61.45 | 73.58 | 73.92 |
| - Stilbene | 1.48 | 3.62 | 3.40 |
| By-products (wt %) | 5.06 | 9.91 | 13.19 |
| - benzaldehyde | 4.73 | 9.41 | 13.19 |
| - benzylalcohol | 0.33 | 0.50 | 0.00 |
| - benzoic acid | 0.00 | 0.00 | 0.00 |
| Unidentified | 2.59 | 12.89 | 9.49 |

EXAMPLES 28–30: TOLUENE COUPLING WITH SODIUM AND AMMONIUM PEROXODISULPHATE

The procedure of Example 1 was repeated replacing potassium peroxodisulphate by sodium peroxodisulphate or ammonium peroxodisulphate, in each case using 0.165 mole of the oxidant. The procedure was modified by the use of only 75 ml of water instead of 500 ml used in Example 1; this was possible because of the greater solubility of these peroxodisulphates. (Reduction of the amount of water even to 150 ml when using potassium peroxodisulphate results in incomplete dissolution of the oxidant). Comparative examples were provided by tests conducted with no additive, and an example of the invention was provided by a test run with the addition 0.08 moles of TEA sulphate.

The results set out in Table 5 show the low selectivity to coupled products achieved by these alternative peroxodisulphates alone, and the greatly enhanced selectivity achieved by the addition of TEA sulphate to ammonium persulphate. This is highly significant in view of the desirability of using the more readily regenerable ammonium peroxodisulphate; without employing the quarternary ammonium salt according to the invention the yield and selectivity to coupled products would make this oxidant impractical.

TABLE 5

| Example | Peroxo- disulphate | Addi- tive (mole) | Reac- tion Time (hr) | Toluene Conver- sion (%) | DPE (wt %) | Coup- ling Selec- tivity (mole %) |
|---|---|---|---|---|---|---|
| Com- parative | | | | | | |
| 28 | Na | — | 1 | 15 | 1.5 | 13 |
| 29 | NH$_4$ | — | 1 | 18 | 2.4 | 23 |
| Invention | | | | | | |
| 30 | NH$_4$ | TEA | 1 | 35 | 24.6 | 76 |

COMPARTIVE EXAMPLE 31a: TOLUENE COUPLING USING CROWN ETHER

Further testing was carried out using the procedure of Example 1 but employing half the amounts of the reactants plus 0.01 mole of a crown ether- 1,4,7,10,13,16-hexaoxacyclooctadecane also known as 18-crown-6- which is normally regarded as a very effective phase transfer catalyst. The results obtained are given in Table 6 and should be compared with Example 1 which uses a reaction mixture having the same proportions of reactants apart from having no crown ether additive. It can be seen that the use of the crown ether results in poorer conversions and gives no improvement in selectivity.

COMPARATIVE EXAMPLE 31b: TOLUENE COUPLING USING CROWN ETHER

A small scale test was carried out using excess crown ether. The procedure of Example 1 was repeated using the following quantities:

50 ml water
1 ml (9.5×10$^{-3}$ mol) toluene
1.27 g (4.1×10$^{-3}$ mol) K$_2$S$_2$O$_8$ and to this was added 25 grams (9.5×10$^{-3}$ mol) of 18-crown-6 thus 17 times the relative amount of crown ether used in Example 31a. The results are given in Table 6 and show low conversion and lower selectivity than Example 31a.

TABLE 6

| Example | 31a | 31b |
|---|---|---|
| Additive | 18-crown-6 | 18-crown-6 (excess) |
| Toluene Conversion (%) | 34 | 39 |
| Products (wt %) | | |
| - DPE | 22.8 | 19.8 |
| - Stilbene | 0.8 | — |
| Benzaldehyde | 8.7 | 14.5 |
| Benzoic acid | 0.0 | 0.0 |
| Coupling Selectivity (mole %)* | 74% | 54% |

*as in Table 1

EXAMPLE 32–42: TOLUENE COUPLING USING POTASSIUM PEROXODISULPHATE AND TMA OR TEA ADDITIVES

A further set of tests were carried out on toluene coupling using potassium peroxodisulphate as oxidant using the following procedure:

500 ml (0.165 mole) of 0.3 M aqueous solution of quarternary ammonium salt were added to a 1 liter 3-neck flask fitted with a reflux condenser stirrer and thermometer. The solution was heated to 40° C. or 80° C. (as indicated) over 15 minutes. 37.7 g (0.165 mole) of potassium peroxodisulphate and 35 ml (0.33 mole) of toluene were added. The mixture was refluxed at 85° C. for one hour with stirring, then cooled to 30°–35° C. and separated for analysis.

Results are given in Table 7.

Example 32 was carried out without quarternary ammonium salt to provide a comparison. Examples 33 and 34 used TEA sulphate as the additive and showed significantly reduced conversion which is not entirely understood but may result from degradation on storage of the TEA hydroxide from which the sulphate was prepared or the degradation of the sulphate during the pre-heating step employed. Examples 35 to 39 used TMA sulphate and show improved conversion and selectivity to coupled products as compared to Example 32. In Example 39 refluxing was continued for 4.5 hours at which stage all peroxodisulphate was converted. In Example 40 the aqueous phase also contained 0.33 mole potassium sulphate, while Example 41 contained 0.5 mole potassium bisulphate to simulate the effect of the build up of spent oxidant, and in each case the selectively was reduced. This indicates the desirability of incorporating a regeneration step in a continuous process to prevent such a build up.

Example 42 was carried out using BTMA sulphate as additive and shows improved conversion and selectivity relative to Example 32.

TABLE 7

| Example | Additive | Preheat (°C.) | Toluene Conversion (%) | Coupling Selectivity[a] (%) |
|---|---|---|---|---|
| 32 | | 40 | 29 | 65 |
| 33 | (TEA)$_2$SO$_4$ | 40 | 15 | 33 |
| 34 | (TEA)$_2$SO$_4$ | 80 | 18 | 20 |
| 35 | (TMA)$_2$SO$_4$ | 40 | 30 | 82 |
| 36 | (TMA)$_2$SO$_4$ | 40 | 38 | 79 |
| 37 | (TMA)$_2$SO$_4$ | 80 | 37 | 78 |
| 38 | (TMA)$_2$SO$_4$ | 80 | 39 | 74 |
| 39[b] | (TMA)$_2$SO$_4$ | 80 | 44 | 77 |
| 40[c] | (TMA)$_2$SO$_4$ | 80 | 32 | 66 |
| 41[d] | (TMA)$_2$SO$_4$ | 80 | 34 | 60 |
| 42 | (BTMA)$_2$SO$_4$ | 40 | 29 | 85 |

Notes:
[a]As in Table 1
[b]Total reflux period was 4.5 hrs.
[c]Aqueous phase contained 0.33 moles of K$_2$SO$_4$ as additive
[d]Aqueous phase contained 0.5 moles of KHSO$_4$ as additive

EXAMPLES 43–48: TOLUENE COUPLING USING AMMONIUM PERSULPHATE AND TMA ADDITIVE

The procedure of Example 32 was repeated replacing potassium persulphate by 0.165 moles of ammonium persulphate. Tetramethylammonium sulphate was employed as the additive in various amounts, and the amount of water was also varied. The results are given in Table 8.

The Examples illustrate the improved selectivity which may be obtained using the process of the invention with ammonium persulphate as oxidant in the presence of TMA. Comparison of Examples 43 and 44 shows that a decrease in the amount of water results in a decrease in selectivity, but a comparison of Examples 44 and 46 shows that this can be more than compensated by an increase in the amount of TMA sulphate to give excellent selectivity even with reduced amounts of water.

Example 47 shows that the presence of fluoride ion in the reaction mixture may be tolerated which may assist regeneration.

Example 48 shows that a longer reaction time results in improved conversion as all peroxodisulphate is consumed.

TABLE 8

| Example | (TMA)$_2$SO$_4$ (moles) | Water Volume (ml) | Toluene Conversion (%) | Coupling Selectivity (Mole %) |
|---|---|---|---|---|
| 43 | 0.15 | 500 | 32–35 | 77 |
| 44 | 0.15 | 180 | 32–35 | 65 |
| 45 | 0.30 | 500 | 32–35 | 85 |
| 46 | 0.30 | 250 | 32–35 | 82 |
| 47[a] | 0.15 | 500 | 32–35 | 79 |
| 48[b] | 0.15 | 500 | 52 | 83 |

Notes:
[a]Aqueous phase contained 1.7 mmole potassium fluoride
[b]Reflux period = 4 hours, at which there was total persulphate conversion.

EXAMPLE 49: DPE to Stilbene

DPE was dehydrogenated in a laboratory scale cracking reactor. The DPE was passed with steam over 30 g of a commercially available dehydrogenation catalyst (Girdler G64C) in the reactor which was maintained at 550°. At 15 minute intervals the output from the reactor was sampled and the sample was analysed in a gas chromatograph. The reactor conditions and the results of the sampling are given in Table 9.

TABLE 9

| Reaction Conditions | | Sampling Time (min.) | DPE Conv. (%) | Stilbene Selectivity (%) | | | Other Components (mass %) | | | |
|---|---|---|---|---|---|---|---|---|---|---|
| LHSV | H$_2$O/HC (mass) | | | cis. | trans. | total | Benzene | Toluene | Unidentified heavier than toluene | Unidentified heavier than trans. stilbene |
| 0.73 | 3.6 | 0.15 | 29.1 | 52.0 | 14.9 | 66.9 | 2.55 | 4.35 | 1.9 | 0.8 |
| 0.90 | 3.4 | 15.30 | 49.0 | 13.2 | 76.5 | 89.7 | 3.55 | 1.55 | — | — |
| 1.30 | 2.5 | 30.45 | 47.0 | 9.6 | 81.2 | 90.8 | 2.6 | 1.7 | — | — |
| 1.31 | 2.5 | 45.60 | 43.0 | 9.3 | 86.2 | 95.5 | 1.2 | 0.55 | — | — |
| 1.33 | 2.3 | 60.75 | 41.5 | 9.4 | 89.1 | 98.5 | — | 0.60 | — | — |
| 1.30 | 2.6 | 75.90 | 41.9 | 9.5 | 90.5 | 100.0 | — | — | — | — |
| 1.09 | 3.2 | 90.105 | 41.7 | 11.2 | 88.8 | 100.0 | — | — | — | — |
| 1.00 | 3.3 | 105.120 | 40.0 | 14.5 | 83.6 | 98.1 | — | — | — | — |
| 0.94 | 3.6 | 120.135 | 41.7 | 13.0 | 84.8 | 97.8 | — | — | — | — |

EXAMPLE 50: DPE TO STILBENE

The procedure of Example 29 was repeated under slightly different reactor conditions and the results obtained are given in Table 10.

The Examples show that the process of the invention enables high conversions of toluene to DPE to be achieved with good selectivity. When compared to conventional coupling reactions under similar conditions of reaction time and temperature, the process of the invention can be seen to give superior selectivity to coupled products. Moreover, the peroxodisuplphate may be regenerated without interference from undesirable metal ions.

TABLE 6

| Sampling Time (min.) | Conditions | | DPE Conv. (%) | Stilbene Selectivity (%) | | | Other Components (mass %) | | |
|---|---|---|---|---|---|---|---|---|---|
| | LHSV | H₂O/HC (mass) | | cis. | trans. | total | Benzene | Toluene | heavier than trans. stilbene |
| 0–15 | 0.93 | 3.9 | 33.1 | 7.4 | 83.4 | 91.8 | 2.55 | 0.55 | None[2] |
| 15–30 | 1.15 | 4.1 | 35.0 | 8.8 | 88.5 | 97.3 | 0.65 | 0.3 | |
| 30–45 | 1.46 | 3.2 | 32.3 | 8.9 | 87.9 | 96.8 | 0.55 | 0.45 | |
| 45–60 | 1.56 | 3.0 | 30.1 | 8.9 | 87.4 | 96.3 | 0.65 | 0.45 | |
| 60–75 | 1.89 | 2.5 | 29.6 | 8.3 | 85.5 | 93.8 | 0.95 | 0.9 | |
| 75.90 | 1.81 | 2.6 | 30.4 | 8.6 | 86.6 | 95.2 | 0.8 | 0.7 | |
| 90–105 | 1.71 | 2.7 | 30.0 | 8.7 | 85.1 | 93.8 | 0.9 | 1.0 | |
| 105–120 | 1.19 | 3.9 | 31.1 | 8.4 | 74.6 | 83.0[1] | 2.3 | 2.8 | |
| 120–135 | 0.46 | 10.2 | 37.6 | 8.5 | 88.1 | 93.6 | 0.8 | 0.45 | |

[1]Unexplained low selectivity to stilbene (0.2 mass % unidentified compound between cis and trans-stilbene).
[2]No heavier compound than trans-stilbene (G.C. column maintained 20 min. at 250° C. after detection trans-stilbene peak) all samples are snow white (solid at room temperature), first sample if only slightly yellow.

We claim:

1. A process for the selective dehydrocoupling of an aromatic compound having a methylidyne group (—CH<) attached to the aromatic nucleus to form dimeric products, in which process the aromatic compound is oxidatively coupled in the liquid phase with a peroxodisulphate in the presence of a quaternary ammonium salt in which the quaternary ammonium cation has substituents selected from the group consisting of methyl, ethyl and benzyl substituents, there being at least 0.2 equivalents of said quaternary ammonium cation per mole of said peroxodisulphate.

2. A process as claimed in claim 1, in which said aromatic compound is selected from the group consisting of toluene and substituted toluenes.

3. A process as claimed in claim 1, in which said peroxodisulphate is ammonium peroxodisulphate.

4. A process as claimed in claim 1, in said quaternary ammonium salt is selected from the group consisting of tetraethylammonium salts, tetramethylammonium salts and benzyltrimethylammonium salts.

5. A process as claimed in claim 4, in which said quaternary ammonium salt is selected from the group consisting of tetramethylammonium sulphate and benzyltrimethylammonium sulphate.

6. A process as claimed in claim 1, in which at least 0.4 equivalents of quaternary ammonium cation per mole of peroxodisulphate are used.

7. A process as claimed in claim 6, in which from 1.0 to 8.0 equivalents of quaternary ammonium cation per mole of peroxodisulphate are used.

8. A process as claimed in claim 7, in which from 1.8 to 4.0 equivalents of quaternary ammonium cation per mole of peroxodisulphate are used.

9. A continuous process for the oxidative dehydrocoupling of aromatic compounds having a methylidyne group (—CH<) attached to the aromatic nucleus to form dimeric products coupled through the methylidyne groups of the constituent aromatic compounds, in which process:

(a) the aromatic compound having a methylidyne group is contacted with an aqueous peroxodisulphate solution in the presence of a quaternary ammonium salt selected from the group consisting of tetramethylammonium salts, tetraethylammonium salts and benzyltrimethylammonium salts, there being at least 0.2 equivalents of quaternary ammonium cation per mole of the peroxodisulphate, to form a mixture of an organic phase comprising dimeric products and an aqueous phase comprising quaternary ammonium salt and reduced forms of the peroxodisulphate;

(b) separating the organic and aqueous phases, and recovering the dimeric products from the organic phase:

(c) subjecting the aqueous phase to electrolysis to regenerate the peroxodisulphate therein; and (d) recycling the aqueous phase comprising regenerated peroxodisulphate and quaternary ammonium salt to step (a).

10. A process as claimed in claim 9, in which the aromatic compound is contacted with ammonium peroxodisulphate in the presence of a quaternary ammonium salt selected from the group consisting of tetramethylammonium sulphate and benzyltrimethylammonium sulphate, there being from 1.0 to 8.0 equivalents of quaternary ammonium cation per mole of ammonium peroxodisulphate.

* * * * *